US006531313B1

(12) United States Patent
Goudsmit et al.

(10) Patent No.: US 6,531,313 B1
(45) Date of Patent: Mar. 11, 2003

(54) INVASIVE BACTERIAL VECTORS FOR EXPRESSING ALPHAVIRUS REPLICONS

(75) Inventors: Jaap Goudsmit, Amsterdam (NL); Jerald C. Sadoff, Bluebell, PA (US); Wayne Koff, Stony Brook, NJ (US)

(73) Assignee: International Aids Vaccine Initiative, New York, NY (US)

( * ) Notice: Subject to any disclaimer, the term of this patent is extended or adjusted under 35 U.S.C. 154(b) by 0 days.

(21) Appl. No.: 09/697,236

(22) Filed: Oct. 26, 2000

Related U.S. Application Data

(60) Provisional application No. 60/161,448, filed on Oct. 26, 1999.

(51) Int. Cl.[7] ........................ C12N 15/85; C12N 15/87; C12N 15/64; A61K 39/12; A61K 39/45

(52) U.S. Cl. .................. 435/320.1; 435/69.1; 435/69.3; 435/71.1; 435/91.4; 435/91.41; 424/200.1; 424/201.1; 424/205.1; 424/206.1; 424/226.1; 424/227.1; 424/228.1; 424/229.1; 424/231.1; 424/188.1; 424/93.2; 424/93.4; 424/93.6

(58) Field of Search ........................... 424/200.1, 201.1, 424/188.1, 206, 189.1, 226.1, 227.1, 228.1, 229.1, 231.1, 93.2, 93.4, 93.6, 205.1; 435/320.1, 69.1, 69.3, 71.1, 91.4, 91.41

(56) References Cited

U.S. PATENT DOCUMENTS

| | | | |
|---|---|---|---|
| 5,739,026 | A | 4/1998 | Garoff et al. |
| 5,766,602 | A | 6/1998 | Xiong et al. |
| 5,789,245 | A | 8/1998 | Dubensky, Jr. et al. |
| 5,792,462 | A | 8/1998 | Johnston et al. |
| 5,814,482 | A | 9/1998 | Dubensky, Jr. et al. |
| 5,824,538 | A | 10/1998 | Branstrom et al. |
| 5,843,723 | A | 12/1998 | Dubensky, Jr. et al. |
| 5,877,159 | A | 3/1999 | Powell et al. |

FOREIGN PATENT DOCUMENTS

| | | |
|---|---|---|
| WO | WO 97/24447 | 7/1997 |

OTHER PUBLICATIONS

Liljestrom et al. Current Biology 1994, vol. 5, pp. 495–500.*

Herweijer et al. Human Gene Ther. 1995, vol. 6, pp. 1161–1167.*

Lunderstorm et al. Current opinion in Biotechnology 1997, vol. 8, pp. 578–582.*

Ascon et al. Oral Immunization with a *Salmonella typhimurium* Vaccine Vector Expressing Recombinant Enterotoxigenic *Escherichia coli* K99 Fimbriae Elicits Elevated Antibody Titers for Protective Immunity. (1998) Infection & Immunity 66(11):5470–5476.

Brossier et al. Antigen delivery by attenuated *Bacillus anthracis*: new prospects in veterinary vaccines. (1999) J. Appl. Microbiol. 87(2):298–302.

Butterton et al. Coexpression of the B Subunit of Shiga Toxin 1 and EaeA from Enterohemorrhagic *Escherichia coli* in *Vibrio cholerae* Vaccine Strains. (1997) Infection & Immunity 65(6):2127–2135.

Cardenas et al. Stability, immunogenicity and expression of foreign antigens in bacterial vaccine vectors. (1993) Vaccine 11(2):126–135.

Catmull et al. Induction of specific cell–mediated immunity in mice by oral immunization with Salmonella expressing *Onchocerca volvulus* glutathione S–transferase. (1999) Vaccine 17(1):31–39.

Dunstan et al. Comparison of the Abilities of Different Attenuated *Salmonella typhimurium* Strains to Elicit Humoral Immune Responses against a Heterologous Antigen. (1998) Infection & Immunity 66(2):732–740.

Fennelly et al. Mucosal DNA Vaccine Immunization Against Measles with a Highly Attenuated *Shigella flexneri* Vector. (1999) The Journal of Immunology 162:1603–1610.

Flynn et al. Generation of a cytotoxic T–lymphocyte response using a Salmonella antigen–delivery system. (1990) Molecular Microbiology 4(12):2111–2118.

Gonzalez et al. *Salmonella typhi* vaccine strain CVD 908 expressing the circumsporozoite protein of *Plasmodium falciparum*; strain construction and safety and immunogenicity in humans. (1994) J. Infect. Dis. 169(4):927–931.

Gonzalez et al. Immunogenicity of a *Salmonella typhi* CVD 908 candidate vaccine strain expressing the major surface protein gp63 of *Leishmania mexicana mexicana*. (1998) Vaccine 16(9–10):1043–1052.

Hartman et al. Construction of a Stable Attenuated *Shigella sonnei* DeltavirG Vaccine Strain, WRSS1, and Protective Efficacy and Immunogenicity in the Guinea Pig Keratoconjunctivitis Model. (1998) Infection & Immunity 66(9):4572–4576.

(List continued on next page.)

*Primary Examiner*—James Housel
*Assistant Examiner*—Bao Qun Li
(74) *Attorney, Agent, or Firm*—Hale and Dorr LLP

(57) ABSTRACT

The present invention is directed to a bacterial delivery system for delivering alphavirus replicon DNA into an animal or animal cells with the replicon encoding one or more heterologous genes to be expressed in the animal or the animal cells. The bacteria are invasive bacteria or attenuated invasive bacteria engineered to contain a DNA vector that encodes the alphavirus replicon in a eukaryotic expression cassette. The heterologous gene can encode an antigen, a therapeutic agent, an immunoregulatory agent, an anti-sense RNA, a catalytic RNA, a protein, a peptide, an antibody or an antigen-binding fragment of an antibody. In a preferred embodiment, the heterologous gene encodes one or more antigens useful as a vaccine for HIV. In addition to the bacterial delivery system, the invention provides methods of introducing and expressing the heterologous gene(s) in animal or animal cells and methods of stimulating or inducing an immune response.

45 Claims, No Drawings

OTHER PUBLICATIONS

Karem et al. Protective immunity against herpes simplex virus (HSV) type 1 following oral administration of recombinant *Salmonella typhimurium* vaccine strains expressing HSV antigens. (1997) J. Gen. Virol. 78(Pt. 2):427–434.

Khan et al. Construction, expression, and immunogenicity of the *Schistosoma mansoni* P28 glutathione S–transferase as a genetic fusion to tetanus toxin in fragment C in a live Aro attenuated vaccine strain . . . (1994) Proc. Natl. Acad. Sci. USA 91:11261–11265.

Krul et al. Induction of an antibody response in mice against human papillomavirus (HPV) type 16 after immunization with HPV recombinant Salmonella strains. (1996) Cancer Immunol. Immunother. 43(1):44–48.

Levine et al. Attenuated Salmonella as live oral vaccines against typhoid fever and as live vectors. (1996) Journal of Biotechnology 44(1–3):193–196.

Lindberg. The History of Live Bacterial Vaccines. (1995) Dev. Biol. Stand. 84:211–219.

Moore et al. Foreign gene expression in *Corynebacterium pseudotuberculosis*: development of a live vaccine vector. (1999) Vaccine 18–5–6:487–497.

Nayak et al. A Live Recombinant Avirulent Oral Salmonella Vaccine Expressing Pneumococcal Surface Protein A Induces Protective Response against *Streptococcus pneumoniae*. (1998) Infection & Immunity 66(8):3744–3751.

Noriega et al. Further Characterization of DeltaaroA DeltavirG *Shigella flexneri* 2a Strain CVD 1203 as a Mucosal Shigella Vaccine and as a Live–Vector Vaccine for Delivering Antigens of Enterotoxigenic *Escherichia coli*. (1996) Infection & Immunity 64(1):23–27.

Paglia et al. Gene Transfer in Dendritic Cells, Induced by Oral DNA Vaccination with *Salmonella typhimurium*, Results in Protective Immunity Against a Murine Fibrosarcoma. (1998) Blood 92(9):3172–3176.

Poirier et al. Protective Immunity Evoked by Oral Administration of Attenuated aroA *Salmonella typhimurium* Expressing Cloned Streptococcal M Protein. (1998) Journal of Experimental Medicine 168(1):25–32.

Ryan et al. Oral Immunization with Attenuated Vaccine Strains of *Vibrio cholerae* Expressing a Dodecapeptide Repeat of the Serine–Rich *Entamoeba histolytica* Protein fused to the Cholera Toxin B Subunit . . . (1997) Infection & Immunity 65(8):3118–3125.

Smerdou et al. Characterization of transmissible gastroenteritis coronavirus S protein expression products in avirulent *S. typhimurium* Deltacya Deltacrp: persistence, stability and immune response in swine. (1996) Veterinary Microbiology 48(1–2):87–100.

Srinivasan et al. Oral Immunization with Attenuated Salmonella Expressing Human Sperm Antigen Induces Antibodies in Serum and the Reproductive Tract. (1995) Biology of Reproduction 53(2):462–471.

Tite et al. Anti–viral immunity induced by recombinant nucleoprotein of influenza A virus. III. Delivery of recombinant nucleoprotein to the immune system using attenuated *Salmonella typhimurium* . . . (1990) Immunology 70(4):540–546.

Viret et al. Expression of *Shigella sonnei* lipopolysaccharide in *Vibrio cholerae*. (1996) Molecular Microbiology 19(5):949–963.

Galen et al. (1997) A Murine Model of Intranasal Immunization to Assess the Immunogenicity of Attenuated Salmonella Typhi Live Vector Vaccines in Stimulating Serum Antibody Responses to Expressed Foreign Antigens, Vaccine 15:700–708.

Harokopakis et al. (1997) Mucosal Immunogenicity of a Recombinant *Salmonella typhimurium*–Cloned Heterologous Antigen in the Absence or Presence of Coexpressed Cholera Toxin A2 and B Subunits, Infect. Immun. 65:1445–1454.

Mestecky J et al. (1997) Routes of Immunization and Antigen Delivery Systems for Optimal Mucosal Immune Response in Humans, Behring Inst. Mitt. 98:33–43.

Pasetti et al. (1999) Attenuated DeltaguaBA Salmonella Typhi Vaccine Strain CVD 915 as a Live Vector Utilizing Prokaryotic or Eukaryotic Expression Systems to Deliver Foreign Antigens and Elicit Immune Responses, Clin. Immunol 92:76–89.

Renauld–Mongenie et al. (1996) Induction of Mucosal Immune Response Against a Heterologous Antigen Fused to Filamentous Hemagglutinin After Intranasal Immunization with Recombinant *Bordetella pertussis* Proc. Natl. Acad. Sci. USA 93: 7944–7949.

Liljequist, et al. (1999) "Production of Recombinant Subunit Vaccines: Protein Immunogens, Live Delivery Systems and Nucleic Acid Vaccines" J. of Biotechnol. 73:1–33.

Berglund, et al. (1988) "Enhancing Immune Responses Using Suicidal DNA Vaccines" Nat. Bio. 16:582–565.

Burdon, et al. (1992) "Fate of Microinjected Genes in Preimplantation Mouse Embryos" Mol. Rep. and Dev. 33:436–442.

Davis, et al., (1993) "DNA–based Immunization Induces Continuous Secretion of Hepatitis B Surface Antigen and High Levels of Circulating Antibody" Hum. Mol. Gen. 2:1847–1851.

Davis, et al., (1994) "Direct Gene Transfer in Skeletal Muscle: Plasmid DNA–based Immunization Against the Hepatitis B Virus Surface Antigen" Vac. 12:1503–1509.

Hariharan, et al., (1998) "DNA Immunization Against Herpes Simplex Virus: Enhanced Efficacy Using a Sindbis Virus–Based Vector" Jour. Of Vir. 72:950–958.

Hoffman, et al., (1994) "Protection Against Malaria by Immunization with a *Plasmodium yoelii* Circumsporozoite Protein Nucleic Acid Vaccine" Vac. 12:1529–1533.

Johnston, et al., (1994) "Gene Gun Transfection of Animal Cells and Genetic Immunization" Meth. Cell Bio. 43:353–365.

Naito, et al. (1994) "Production of Germline Chimeric Chickens, with High Transmission Rate of Donor–Derived Gametes, Produced by Transfer of Primordial Germ Cells" Mol. Rep. and Dev. 39:153–161.

Polo, et al. (1998) "DNA Vaccines with a Kick" Nat. Bio. 16:517–518.

Robinson, et al. (1993) "Protection Against a Lethal Influenza Virus Challenge by Immunization with a Haemagglutinin–Expressing Plasmid DNA" Vac. 11:957–960.

Watanabe, et al., (1994) "Liposome–Mediated DNA Transfer Into Chicken Primordial Germ Cells In Vivo" Mol. Rep. and Dev. 38:268–274.

Webster, et al. (1994) "Protection of Ferrets Against Influenza Challenge with a DNA Vaccine to the Haemagglutinin" Vac. 12:1495–1498.

Xiang, et al. (1994) "Vaccination with a Plasmid Vector Carrying the Rabies Virus Glycoprotein Gene Induces Protective Immunity Against Rabies Virus" Viro. 199:132–140.

* cited by examiner

INVASIVE BACTERIAL VECTORS FOR EXPRESSING ALPHAVIRUS REPLICONS

This application claims the benefit of Provisional Application No. 60/161,448 filed Oct. 26, 1999.

FIELD OF THE INVENTION

The present invention is directed to a bacterial delivery system for delivering alphavirus replicon DNA into an animal or animal cells with the replicon encoding one or more heterologous genes to be expressed in the animal or the animal cells. The bacteria are invasive bacteria or attenuated invasive bacteria engineered to contain a DNA vector that encodes the alphavirus replicon in a eukaryotic expression cassette. Upon bacterial infection, primary transcription of the DNA vector is driven by the eukaryotic expression vector and produces an alphavirus replicon RNA which is transported to the cytoplasm. That RNA is transcribed, and translated if the gene encodes a protein, to express the heterologous gene encoded in the alphavirus replicon. The heterologous gene may encode an antigen, a therapeutic agent, an immunoregulatory agent, an anti-sense RNA, a catalytic RNA, a protein, a peptide, an antibody, an antigen-binding fragment of an antibody or any other molecule desired for delivery to an animal or animal cell. In a preferred embodiment, the heterologous gene encodes one or more antigens useful as a vaccine for HIV. In addition to the bacterial delivery system, the invention provides methods of introducing and expressing the heterologous gene(s) in animal or animal cells, methods of stimulating or inducing an immune response and vaccines therefor.

BACKGROUND OF THE INVENTION

There are many applications for delivering DNA to animals or animal cells including for gene therapy of acquired or inherited diseases or conditions, for DNA-based vaccination, for understanding genetic structure and for studying the molecular mechanisms underlying gene expression.

Successful delivery of DNA to animal tissue has been achieved by cationic liposomes [Watanabe et al., Mol. Reprod. Dev. 38:268–274 (1994)], direct injection of naked DNA into animal muscle tissue [Robinson et al., Vacc. 11:957–960 (1993); Hoffman et al., Vacc. 12:1529–1533; (1994); Xiang et al., Virol. 199:132–140 (1994); Webster et al., Vacc. 12:1495–1498 (1994); Davis et al., Vacc. 12:1503–1509 (1994); and Davis et al., Hum. Molec. Gen. 2:1847–1851 (1993)], and embryos [Naito et al., Mol. Reprod. Dev. 39:153–161 (1994); and Burdon et al., Mol. Reprod. Dev. 33:436–442 (1992)], or intradermal injection of DNA using "gene gun" technology [Johnston et al., Meth. Cell Biol. 43:353–365 (1994)]. A limitation of these techniques is that they only efficiently deliver DNA to parenteral sites. At present, effective delivery of eukaryotic expression cassettes to mucosal tissue has been met with limited success. This is presumably due to poor access to these sites, toxicity of the delivery vehicles or instability of the delivery vehicles when delivered orally.

For DNA-based vaccination, delivery by injection of naked plasmid DNA has shown potential in mouse models for inducing both humoral and cellular immune responses. However, in larger animals, using DNA delivery for vaccination has been hampered by requiring large amounts of DNA or inducing persistent expression of an antigen with the potential for developing tolerance to the antigen. Berglund reported a strategy for inducing or enhancing an immune response by injecting mice with plasmid DNA containing an alphavirus DNA expression vector having a recombinant Semliki Forest Virus (SFV) replicon in a eukaryotic expression cassette [Berglund et al., Nature Biotechnol. 16:562–565 (1998)]. The eukaryotic expression cassette controlled expression of the primary nuclear transcription of the SFV replicon. This SFV replicon transcript, encoding the heterologous antigen, was transported to the cytoplasm and amplified by the self-encoded SFV replicase complex. The amplified RNA replicon lead to high level production of an mRNA encoding the heterologous antigen. Similar results were described by Polo and his group [Polo et al., Nature Biotechnol. 16:517–518 (1998); Hariharan et al., J. Virol. 72:950–958 (1998)]. Both groups found strong immune responses could be induced using small amounts of input plasmid DNA. Although this method allows greater expression from the input DNA vector, the method still has the disadvantages associated with parenteral delivery.

Alternatively, a method to deliver DNA to animals that overcomes the disadvantages of conventional delivery methods is by administering attenuated, invasive bacteria containing a bacterial DNA vector having a eukaryotic expression cassette encoding the gene to be expressed. For example, U.S. Pat. No. 5,877,159 to Powell et al., describes live bacteria that can invade animal cells without establishing a productive infection or causing disease to thereby introduce a eukaryotic expression cassette encoding an antigen capable of being expressed by the animal cells. While this method allows delivery of the DNA vaccine to mucosal surfaces and is easy to administer, a concern for vaccine delivery in developing countries, it does not have the advantage of providing amplifiable mRNA encoding the gene of interest.

Accordingly, the present invention combines use of live, attenuated invasive bacteria with a eukaryotic expression cassette encoding an alphavirus replicon to provide improved bacterial delivery systems to deliver one or more heterologous genes to an animal. Such systems have the advantages of both bacterial delivery systems and alphavirus replicon vectors and are efficacious, cost effective and safe. The bacterial delivery systems of the invention are particularly useful for delivering DNA for gene therapy and vaccinations.

All cited references and patents are incorporated by reference herein in their entirety.

SUMMARY OF THE INVENTION

In accordance with the invention, one embodiment is directed to a bacterial delivery system which comprises a live, invasive bacteria containing a DNA comprising a eukaryotic expression cassette operably linked to an alphavirus replicon DNA capable of amplification as RNA in animal cells, wherein the alphavirus replicon DNA comprises at least one nucleic acid control sequence operably linked to a heterologous nucleic acid sequence to control expression of the heterologous nucleic acid sequence. The live invasive bacteria of the invention are attenuated as needed so long as the bacteria delivered into animals either does not make the animal sick or, at most, causes a self-limiting infection that is clinically innocuous in the animal.

The heterologous nucleic acid sequence can encode an antigen, an antigenic fragment of a protein, a therapeutic agent, an immunoregulatory agent, an anti-sense RNA, a catalytic RNA, a protein, a peptide , an antibody, an antigen binding fragment of an antibody, or any other molecule encodable by DNA and desired for delivery to an animal or animal cell. The heterologous nucleic acid sequence can be obtained from a virus selected from the group consisting of influenza virus, respiratory syncytial virus, HPV, HBV, HCV, HIV, HSV, FeLV, FIV, HTLV-I, HTLV-II, and CMV. The viral sequence can encode one or more viral genes or antigenic fragments thereof. The heterologous nucleotide sequence can encode a cytokine, an interleukin, erythropoietin or other immunostimulatory or immunoregulatory protein.

Another embodiment of this invention is directed to a method for introducing and expressing a gene in an animal by infecting the animal with live, invasive bacteria, preferably attenuated invasive bacteria. These bacteria contain a DNA comprising a eukaryotic expression cassette having an alphavirus replicon DNA capable of amplification as RNA in cells of the animal. Further, the alphavirus replicon DNA directs expression of the one or more heterologous nucleic acid sequences which encode the gene product to be expressed in the animal. The method is applicable to deliver genes encoding an antigen, an antigenic protein fragment, a therapeutic agent, an immunoregulatory agent, an anti-sense RNA, a catalytic RNA, a protein, a peptide, an antibody, an antigen-binding fragment of an antibody or any other molecule encodable by DNA and desired for delivery to an animal or an animal cell.

Another aspect of the invention provides a method for inducing an immune response in an animal which by infecting the animal with live, invasive bacteria containing a DNA comprising a eukaryotic expression cassette operably linked to an alphavirus replicon DNA capable of amplification as RNA in animal cells, wherein the alphavirus replicon DNA encodes at least one antigen or antigenic fragment of a protein. The antigen or antigenic fragment are expressed at a level sufficient to stimulate an immune response to the antigen or antigenic fragment. In a preferred embodiment, the antigen is derived from a virus, and more preferably from an HIV virus. This method provides a means to immunize animals, preferably humans, against HIV infection. In a preferred embodiment the, the alphavirus replicon DNA encodes at least one antigen or antigenic fragment from each of the HIV genes env, gag, pol, nef, tat and rev.

Yet another aspect of the invention relates to a method for introducing and expressing a gene in animal cells by (a) infecting animal cells with live, invasive bacteria containing one or more DNA molecules, wherein the DNA molecules comprise a eukaryotic expression cassette operably linked to an alphavirus replicon DNA capable of amplification as RNA in the animal cells and the alphavirus replicon in turn comprises at least one nucleic acid control sequence operably linked to a heterologous nucleic acid sequence to control expression thereof; and (b) culturing those cells under conditions sufficient to express a gene product encoded by said heterologous nucleic acid sequence.

DETAILED DESCRIPTION OF THE INVENTION

As used herein, "invasive bacteria" are bacteria that are capable of delivering eukaryotic expression cassettes to animal cells or animal tissue. "Invasive bacteria" include bacteria that are naturally capable of entering the cytoplasm or nucleus of animal cells, as well as bacteria that are genetically engineered to enter the cytoplasm or nucleus of animal cells or cells in animal tissue. The invasive bacteria of the invention infect the host without establishing a productive infection and/or causing disease in the infected host. In instances where an invasive strains could cause disease or create a problem or health risk for the animal, that strain can be modified, or attenuated, so that it is useful in the invention. Thus, "attenuated, invasive bacteria" are invasive bacteria of the invention, also capable of infecting an animal host without establishing a productive infection and/or causing disease in the infected host. At most an attenuated bacterial strain may cause a self-limiting, clinically-insignificant infection. Attenuation generally refers to a diminished infectious capacity relative to a reference strain.

Thus, attenuated bacteria of the invention can be prepared by methods known in the art. For example, attenuating mutations can be introduced into bacterial pathogens using non-specific mutagenesis either chemically, using agents such as N-methyl-N'-nitro-N-nitrosoguanidine, or using recombinant DNA techniques; classic genetic techniques, such as Tn10 mutagenesis, P22-mediated transduction, lambda-phage mediated crossover, and conjugational transfer; or site-directed mutagenesis using recombinant DNA techniques. Recombinant DNA techniques are preferable. Examples of such attenuating mutations include, but are not limited to:

(i) auxotrophic mutations, such as aro [Hoiseth et al., Nature, 291:238–239 (1981)], gua [McFarland et al., Microbiol. Path. 3:129–141 (1987)], nad (Park et al., J. Bact. 170:3725–3730 (1988), thy [Nnalue et al., Infect. Immun. 55:955–962 (1987)], and asd [Curtiss, et al., Dev. Biol. Stand. 82: 23–33 (1994)]) mutations;

(ii) mutations that inactivate global regulatory functions, such as cya [Curtiss et al., Infect. Immun. 55:3035–3043 (1987)], crp [Curtiss et al (1987), supra], phoP/phoQ [Groisman et al., Proc. Natl. Acad. Sci. USA 86:7077–7081 (1989); and Miller et al., Proc. Natl. Acad. Sci. USA 86:5054–5058 (1989)], $phoP^c$ [Miller et al., *J. Bact.* 172:2485–2490 (1990)] or ompR [Dorman et al., Infect. Immun. 57:2136–2140 (1989)] mutations;

(iii) mutations that modify the stress response, such as recA [Buchmeier et al., Mol. Micro. 7:933–936 (1993)], htrA [Johnson et al., Mol. Micro. 5:401–407 (1991)], htpR [Neidhardt et al., supra, 1981], hsp [Neidhardt et al., supra, 1984] and groEL [Buchmeier et al., Science. 248:730–732 (1990)] mutations;

(iv) mutations in specific virulence factors, such as lsyA [Libby et al., Proc. Natl. Acad. Sci. USA 91:489–493 (1994)], pag or prg [Miller et al, (1990), supra; and Miller et al., (1989), supra), iscA or virG [d'Hauteville et al., Mol. Micro. 6:833–841 (1992)], plcA [Mengaud et al., Mol. Microbiol. 5:367–72 (1991); Camilli et al., J. Exp. Med 173:751–754 (1991)], and act (Brundage et al., Proc. Natl. Acad. Sci. USA 90:11890–11894 (1993)] mutations;

(v) mutations that affect DNA topology, such as topA [Galan et al., Infect. Immun. 58:1879–1885 (1990)] mutation;

(vi) mutations that block biogenesis of surface polysaccharides, such as rfb, galE [Hone et al., J. Infect. Dis. 156:164–167 (1987)] or via [Popoff et al., J. Gen. Microbiol. 138:297–304 (1992)] mutations;

(vii) mutations that modify suicide systems, such as sacB [Recorbet et al., App. Environ. Micro. 59:1361–1366 (1993); Quandt et al., Gene 127:15–21 (1993)], nuc [Ahrenholtz et al., App. Environ. Micro. 60:3746–3751 (1994)], hok, gef, kil, or phlA [Molin et al., Ann. Rev. Microbiol. 47:139–166 (1993)] mutations;

(viii) mutations that introduce suicide systems, such as lysogens encoded by P22 [Rennell et al., Virol.

143:280–289 (1985)], lambda murein transglycosylase [Bienkowska-Szewczyk et al., Mol. Gen. Genet. 184:111–114 (1981)] or S-gene [Reader et al., Virol. 43:623–628 (1971)]; and (ix) mutations that disrupt or modify the correct cell cycle, such as minB [de Boer et al., Cell 56:641–649 (1989)] mutation.

The attenuating mutations can be either constitutively expressed or under the control of inducible promoters, such as the temperature sensitive heat shock family of promoters [Neidhardt et al., 1984, supra], or the anaerobically induced nirB promoter [Harborne et al., Mol. Micro. 6:2805–2813 (1992)] or repressible promoters, such as uapA [Gorfinkiel et al., J. Biol. Chem. 268:23376–23381 (1993)] or gcv [Stauffer et al., J. Bact. 176:6159–6164 (1994)].

The particular naturally occurring invasive bacteria (or attenuated, invasive bacteria) employed in the present invention is not critical thereto. One of ordinary skill in the art can readily determine which bacterial strains are appropriate for use with the animal or animal cells intended to be infected based on the animal's or cells' susceptibility to infection by different bacterial species. Examples of such naturally-occurring invasive bacteria include, but are not limited to, Salmonella spp. Shigella spp., Listeria spp., Rickettsia spp. and enteroinvasive *E. coli.* Any of these strains can be attenuated if needed using known methods.

Examples of Shigella strains which can be employed in the present invention include, but are not limited to, *Shigella flexneri* 2a (ATCC No. 29903), *Shigella sonnei* (ATCC No. 29930), and *Shigella disenteriae* (ATCC No. 13313). An attenuated Shigella strain, such as *Shigella flexneri* 2a 2457T Δ aroA Δ virG mutant CVD 1203 [Noriega et al., Infect. Immun. 62:5168–5172 (1994)], *Shigella flexneri* M90T Δ icsA mutant [Goldberg et al., Infect. Inmun. 62:5664–5668 (1994)], *Shigella flexneri* Y SFL114 aroD mutant [Karnell et al., Vacc. 10:167–174 (1992)], and *Shigella flexneri* Δ aroA Δ aroD mutant [Verma et al., Vacc. 9:6–9 (1991)] are preferably employed in the present invention. Alternatively, new attenuated Shigella spp. strains can be constructed by introducing an attenuating mutation either singularly or in conjunction with one or more additional attenuating mutations.

Examples of Listeria strains which can be employed in the present invention include *Listeria monocytogenes* (ATCC No. 15313). Attenuated Listeria strains, such as *L. monocytogenes* Δ actA mutant (Brundage et al., supra) or *L. monocytogenes* Δ plcA [Camilli et al., J. Exp. Med. 173:751–754 (1991)] are preferably used in the present invention. Alternatively, new attenuated Listeria strains can be constructed by introducing one or more attenuating mutations as described for Shigella spp. above.

Examples of Rickettsia strains which can be employed in the present invention include *Rickettsia rickettsiae* (ATCC Nos. VR149 and VR891), *Rickettsia prowaseckii* (ATCC No. VR233), *Rickettsia tsutsugamuchi* (ATCC Nos. VR312, VR150 and VR609), *Rickettsia mooseri* (ATCC No. VR144), *Rickettsia sibirica* (ATCC No. VR151), and *Rochalimaea quitana* (ATCC No. VR358). Attenuated Ricketsia strains are preferably used in the present invention and can be constructed by introducing one or more attenuating mutations as described for Shigella spp. above.

Examples of *E. coli* strains which can be employed in the present invention include *E. coli* strains 4608-58, 1184-68, 53638-C-17, 13-80, and 6-81 [Sansonetti et al., Ann. Microbiol. (Inst. Pasteur) 132A:351–355 (1982)]. Attenuated enteroinvasive *E. coli* strains are preferably used in the present invention and can be constructed by introducing one or more attenuating mutations as described for Shigella spp. above.

Examples of Salmonella strains which can be employed in the present invention include *Salmonella typhi* (ATCC No. 7251) and *Salmonella typhimurium* (ATCC No. 13311). Attenuated Salmonella strains are preferably used in the present invention and include *S. typhi* aro AaroD [Hone et al., Vacc., 9:810–816 (1991)] and *Salmonella typhimurium* aroA mutant [Mastroeni et al., Micro. Pathol. 13:477–491 (1992)]. Alternatively, new attenuated Salmonella strains can be constructed by introducing one or more attenuating mutations as described for Shigella spp. above.

Examples of additional bacteria which can be genetically engineered to be invasive include, but are not limited to, Yersinia spp., Escherichia spp., Klebsiella spp., Bordetella spp., Neisseria spp., Aeromonas spp., Franciesella spp., Corynebacterium spp., Citrobacter spp., Chlamydia spp., Hemophilus spp., Brucella spp., Mycobacterium spp., Legionella spp., Rhodococcus spp., Pseudomonas spp., Helicobacter spp., Salmonella spp., Vibrio spp., Bacillus spp., and Erysipelothrix spp. These organisms can be engineered to mimic the invasion properties of Shigella spp., Listeria spp., Rickettsia spp., or enteroinvasive *E. coli* by inserting genes that enable them to access the cytoplasm of an animal cell. Specific examples of useful strains from these bacteria are found in U.S. Pat. No. 5,877,159. Additionally, *Mycobacterium bovis* BCG is a useful strait that can be engineered for the invention.

Examples of genes that enable bacteria to access the cytoplasm of a cell include the invasive proteins of Shigella, hemolysin or the invasion plasmid of Escherichia, or listeriolysin O of Listeria. Introducing such genes are known to result in strains that are capable of entering the cytoplasm of infected animal cells [Formal et al., Infect. Immun. 46:465 (1984); Bielecki et al., Nature 345:175–176 (1990); Small et al., In: Microbiology-1986, pages 121–124, Levine et al., Eds. American Society for Microbiology, Washington, D.C. (1986); and Zychlinsky et al., Molec. Micro. 11:619–627 (1994)]. Any gene or combination of genes, from one or more sources, that mediates entry into the cytoplasm of animal cells suffices. Thus, such genes are not limited to bacterial genes, but rather can include viral genes such as influenza virus hemagglutinin HA-2, which promotes endosmolysis [Plank et al., J. Biol. Chem. 269:12918–12924 (1994)].

The above invasive genes can be introduced into the target strain using chromosome or plasmid mobilization [Miller, A Short Course in Bacterial Genetics, Cold Spring Harbor Laboratory Press, Cold Spring Harbor, N.Y. (1992); Bothwell et al., Methods for Cloning and Analysis of Eukaryotic Genes, Eds., Jones and Bartlett Publishers Inc., Boston, Mass. (1990); and Ausubel et al., Short Protocols in Molecular Biology, John Wiley and Sons, New York, N.Y. (1992); bacteriophage-mediated transduction [de Boer et al., Cell, 56:641–649 (1989); Miller (1992), supra; and Ausubel et al., supra], or chemical [Bothwell et al., supra; Ausubel et al., supra; Felgner et al., Proc. Natl. Acad. Sci. USA 84:7413–7417 (1987); and Farhood, Annal. N.Y. Acad. Sci. 716:23–34 (1994)], electroporation [Bothwell et al., supra; Ausubel et al., supra; and Sambrook, Molecular Cloning: A Laboratory Manual, Cold Spring Harbor Laboratory Press, Cold Spring Harbor, N.Y.] and physical transformation techniques [Johnston et al., supra; and Bothwell et al., supra]. The genes can be incorporated on bacteriophage (de Boer et al., supra], plasmids vectors [Curtiss et al. (1987) or Curtiss et al. (1994), supra] or spliced into the chromosome [Hone et al., supra, (1987)] of the target strain.

Furthermore, the bacteria for use in the invention can be modified to increase their ability to infect mucosal surfaces and tissues in an animal. Such modifications permit the bacteria to circumvent natural host barriers. Methods for constructing such bacteria are described in U.S. Pat. No. 5,877,159.

In accordance with the invention the invasive or attenuated invasive bacteria contain a DNA comprising a eukaryotic expression cassette operably linked to an alphavirus replicon DNA. A eukaryotic expression cassette is usually in the form of a plasmid which contains elements needed for transcription of the alphavirus replicon DNA and transport from the nucleus into the cytoplasm. For example, RNA polymerase II cassettes provide the needed control and regulatory elements. Hence, the elements for transcription and transport may include, but are not limited to, promoters active in eukaryotic cells, enhancers, transcription termination signals including polyadenylation signals or polyA tracts, elements to facilitate nucleocytoplasmic transport, elements to facilitate processing of the 3' alphavirus replicon RNA into an authentic virus-like RNA 3' ends and the like.

Hence, the particular eukaryotic cassette employed in the present invention is not critical thereto, and can be selected from, e.g., any of the many commercially available cassettes, such as pCEP4 or pRc/RSV from Invitrogen Corporation (San Diego, Calif.), pXT1, pSG5, pPbac or pMbac from Stratagene (La Jolla, Calif.), pPUR or pMAM from ClonTech (Palo Alto, Calif.), and pSVβ-gal from Promega Corporation (Madison, Wis.), or synthesized either de novo or by adaptation of a publically or commercially available eukaryotic expression system.

The individual elements within the eukaryotic expression cassette can be derived from multiple sources and may be selected to confer specificity in sites of action or longevity of the cassettes in the recipient cell. Such manipulation of the eukaryotic expression cassette can be done by any standard molecular biology approach.

Various promoters are well-known to be useful for driving expression of genes in animal cells, such as the viral-derived SV40, CMV immediate early and, RSV promoters or eukaryotic-derived β-casein, uteroglobin, β-actin or tyrosinase promoters. The particular promoter is not critical to the invention, unless the object is to obtain tissue-specific expression. In this case, a promoter can be selected which is only active in the desired tissue or selected cell type. Examples of tissue-specific promoters include, but are not limited to, αS1- and βcasein promoters which are specific for mammary tissue [Platenburg et al., Trans. Res. 3:99–108 (1994); and Maga et al., Trans. Res. 3:36–42 (1994)]; the phosphoenolpyruvate carboxykinase promoter which is active in liver, kidney, adipose, jejunum and mammary tissue [McGrane et al., J. Reprod. Fert. 41:17–23 (1990)]; the tyrosinase promoter which is active in lung and spleen cells, but not testes, brain, heart, liver or kidney [Vile et al., Canc. Res. 54:6228–6234 (1994)]; the involucerin promoter which is only active in differentiating keratinocytes of the squamous epithelia [Carroll et al., J. Cell Sci., 103:925–930 (1992)]; and the uteroglobin promoter which is active in lung and endometrium [Helftenbein et al., Annal. N.Y. Acad. Sci. 622:69–79 (1991)].

Alternatively, cell-specific enhancer sequences can be used to control expression. For example, human neurotropic papovirus JCV enhancer regulates viral transcription in glial cells alone [Remenick et al., J. Virol. 65:5641–5646 (1991)]. Yet another way to control tissue specific expression is to use a hormone responsive element (HRE) to specify which cell lineages a promoter will be active in, for example, the MMTV promoter requires the binding of a hormone receptor, such as progesterone receptor, to an upstream HRE before it is activated [Beato, FASEB J. 5:2044–2051 (1991); and Truss et al., J. Steroid Biochem. Mol. Biol. 41:241–248 (1992)].

Suitable transcription termination elements include the SV 40 transcription termination region and terminators derived therefrom.

Additional examples of eukaryotic expression cassettes and/or regulatory elements suitable for expressing alphavirus replicon DNA are described in U.S. Pat. Nos. 5,824,538 and 5,877,159.

The bacteria of the bacterial delivery systems can contain one or more eukaryotic expression cassettes operably linked to an alphavirus replicon. Such cassettes can be provided on the same or different plasmids or DNA molecules contained in the bacteria. In some instances it may be desirable for the eukaryotic expression cassette to be integrated into the bacterial chromosome or other episomal DNA and such embodiments are included in the scope of the invention.

Alphavirus are from the Togavirus family and are well known in the art. There are 26 known viruses and virus subtype classified using the hemagglutination assay. See, e.g., U.S. Pat. No. 5,843,723 for list of the many of the alphaviruses. The commonly studied alphaviruses include Sindbis, SFV, Venezuelan equine encephalitis virus (VEE) and Ross River virus. The morphogenesis of the viruses is fairly uniform and the virions are small enveloped, 60–65 nm particles of positive-strand RNA. The genomic RNA (49S RNA) of alphaviruses is approximately 11–12 kb in length, and contains a 5' cap and a 3' polyadenylate tail. Infectious enveloped virus is produced by assembling viral nucleocapsid proteins onto genomic RNA in the cytoplasm, and budding through the cell membrane which has viral-encoded glycoproteins embedded within it. During viral replication, the genomic 49S RNA serves as template for synthesis of a complementary negative strand. The negative strand in turn serves as template for full-length genomic RNA and for an internally initiated, positive-strand 26S subgenomic RNA. The nonstructural proteins are translated from the genomic RNA. Alphaviral structural proteins are translated from the subgenomic 26S RNA. All viral proteins are first synthesized as polyproteins and processed into individual proteins by post-translational proteolytic cleavage.

As used herein, in "alphavirus replicon" of the present invention is used interchangeably to refer to RNA or DNA comprising those portions of the alphavirus genome RNA essential for transcription and export of a primary RNA transcript from the cell nucleus to the cytoplasm, for cytoplasmic amplification of the transported RNA and for subgenomic RNA expression of a heterologous nucleic acid sequence. Thus, the replicon encodes and expresses those nonstructural proteins needed for cytoplasmic amplification of the alphavirus RNA and expression of the subgenomic RNA. It is further preferable that the alphavirus replicon can not be encapsidated to produce alphavirus particles or virions. This can be achieved by replicons which lack one or more of the alphavirus structural genes, and preferably all of the structural genes. In a preferred embodiment, alphavirus replicons of the invention are capable of being transcribed from a eukaryotic expression cassette and processed into RNA molecules with authentic alphavirus-like 5' and 3' ends.

Alphavirus replicons and expression vectors containing them are well known in the art and many vectors containing a wide range of alphavirus replicons have been described. Examples of such replicons can be found, e.g., in U.S. Pat. Nos. 5,739,026; 5,766,602; 5,789,245; 5,792,462; 5,814, 482; and 5,843,723 and in Polo, supra, and Berglund, supra. While many of the features of these alphavirus replicons are useful for the present invention not all of them are essential for the reasons set forth above. So long as a portion of the alphavirus replicon does not interfere with production of the primary RNA transcript, cytoplasmic amplification thereof and expression of the heterologous nucleic acid sequence, such portions can remain as part of the replicon. Those skilled in the art can readily determine the nature of and remove any unnecessary or interfering sequences.

The patents and references set forth above also describe representative methods for constructing and producing the alphavirus replicons of the invention. Alphavirus replicons can be prepared from any alphavirus or any mixture of alphavirus nucleic acid sequences. In this regard the preferred alphavirus replicons are derived from Sindbis virus, SFV, VEE or Ross River virus.

The alphavirus replicons can be incorporated as DNA into eukaryotic expression cassettes using recombinant DNA techniques conventional in the art.

In accordance with the invention, the alphavirus replicon comprises nucleic acid control sequences operably linked to a heterologous nucleic acid sequence to control expression thereof. These control sequences are sequence elements to control transcription and translation as needed. The sequence elements can include, but are not limited to, promoters, enhancers, transcription, termination signals, translation start sites and the like. These elements can be the same as or different from those described herein for the eukaryotic expression cassette. In some cases, the same sequence elements can be used in the eukaryotic expression cassettes and as a sequence element to control expression of the heterologous nucleic acid.

As used herein, "heterologous" refers to the relationship between the source of the alphavirus replicon and the source of the heterologous nucleic acid sequence. Thus, the heterologous nucleic acid sequence does not encode an alphavirus gene but rather encodes a gene that is either foreign or endogenous to the animal cells that have been infected with the bacterial delivery system of the invention. As used herein, "foreign gene or nucleic acid sequence" means a gene or a nucleic acid sequence encoding a protein or fragment thereof or anti-sense RNA or catalytic RNA, which is foreign to the recipient animal cell or tissue, such as a vaccine antigen, immunoregulatory agent, or therapeutic agent. An "endogenous gene or nucleic acid sequence" means a gene or a nucleic acid sequence encoding a protein or part thereof or anti-sense RNA or catalytic RNA which is naturally present in the recipient animal, animal cell or tissue.

The heterologous nucleic acid sequence cqan be constructed from naturally-occurring gene sequences or synthetically-constructed gene sequences.

The heterologous nucleic acid sequence, or interchangeably, heterologous gene, can encode an antigen, an antigenic fragment of a protein, a therapeutic agent, an immunoregulatory agent, an anti-sense RNA, a catalytic RNA, a protein, a peptide, an antibody, an antigen-binding fragment of an antibody, or any other molecule encodable by DNA and desired for delivery to an animal or animal cell. The heterologous nucleic acid sequences can be obtained from a virus selected from the group consisting of influenza virus, respiratory syncytial virus, HPV, HBV, HCV, HIV, HSV, FeLV, FIV, HTLV-I, HTLV-II, and CMV. These abbreviations are used for these following viruses: HPV, human papilloma virus; HBV, hepatitis B virus; HCB, hepatitis C virus; HIV, human immunofediciency virus; HSV, herpes simplex viruses; FeLV, feline leukemia virus; FIV, feline immunodeficiency virus; HTLV-I, human T-lymphotrophic virus I; HTLV-II, human T-lymphotrophic virus II; and CMV, cytomegalovirus.

The viral sequences can encode one or more viral genes or antigenic fragments thereof. The heterologous nucleotide sequence can also encode a cytokine, an interleukin, erythropoietin, or other immunostimulatory or immunoregulatory protein.

The antigen may be a protein or antigenic fragment thereof from viral pathogens, bacterial pathogens, and parasitic pathogens. Alternatively, the antigen may be a synthetic gene, constructed using recombinant DNA methods, which encode antigens or parts thereof from viral, bacterial, parasitic pathogens. These pathogens can be infectious in humans, domestic animals or wild animal hosts.

The antigen can be any molecule that is expressed by any viral, bacterial, parasitic pathogen prior to or during entry into, colonization of, or replication in their animal host.

Single or multiple eukaryotic expression cassettes can be delivered that express any combination of viral, bacterial, parasitic antigens, or synthetic genes encoding all or parts or any combination of viral, bacterial, parasitic antigens.

The viral pathogens, from which the viral antigens are derived, include, but are not limited to, Orthomyxoviruses, such as influenza virus; Retroviruses, such as RSV and SIV, Herpesviruses, such as EBV, CMV or herpes simplex virus; Lentiviruses, such as human immunodeficiency virus; Rhabdoviruses, such as rabies; Picornoviruses, such as poliovirus; Poxviruses, such as vaccinia; Rotavirus; and Parvoviruses. Examples of protective antigens of viral pathogens include the HIV antigens nef, p24, gp120, gp41, gp160, env, gag, tat, rev, and pol [Ratner et al., Nature 313:277–280 (1985)] and T cell and B cell epitopes of gp120 [Palker et al., J. Immunol. 142:3612–3619 (1989)]; the hepatitis B surface antigen [Wu et al., Proc. Natl. Acad. Sci. USA 86:4726–4730 (1989)]; rotavirus antigens, such as VP4 and VP7 [Mackow et al., Proc. Natl. Acad. Sci. USA 87:518–522 (1990); Green et al., J. Virol. 62:1819–1823 (1988)], influenza virus antigens such as hemagglutinin or nucleoprotein (Robinson et al., supra; Webster et al., supra) and herpes simplex virus thymidine kinase (Whitley et al., In: New Generation Vaccines, pages 825–854). In the case of HIV, the antigens can be from any structural, accessory or regulatory gene, and includes combinations or chimeras of such genes in multiple or single alphavirus replicons. In a preferred embodiment, the heterologous gene encodes at least one antigen or antigenic fragment from each of the HIV genes env, gag, pol, nef, tat, and rev.

The bacterial pathogens, from which the bacterial antigens are derived, include but are not limited to, Mycobacterium spp., *Helicobacter pylori,* Salmonella spp., Shigella spp., *E. coli,* Rickettsia spp., Listeria spp., *Legionella pneumoniae,* Pseudomonas spp., Vibrio spp., and *Borellia burgdorferi.*

Examples of protective antigens of bacterial pathogens include the *Shigella sonnei* form 1 antigen [Formal et al., Infect. Immun. 34:746–750 (1981)]; the O-antigen of *V. cholerae* Inaba strain 569B [Forrest et al., J. Infect. Dis. 159:145–146 (1989); protective antigens of enterotoxigenic *E. coli,* such as the CFA/I fimbrial antigen [Yamamoto et al., Infect. Immun. 50:925–928 (1985)] and the nontoxic B-subunit of the heat-labile toxin [Clements et al., Infect. Immun. 46:564–569 (1984)]; pertactin of *Bordetella pertussis* [Roberts et al., Vacc. 10:43–48 (1992)], adenylate cyclase-hemolysin of *B. pertussis* [Guiso et al., Micro. Path. 11:423–431 (1991)], and fragment C of tetanus toxin of

*Clostridium tetani* [Fairweather et al., Infect. Immun. 58:1323–1326 (1990)].

The parasitic pathogens, from which the parasitic antigens are derived, include but are not limited to, Plasmodium spp., Trypanosome spp., Giardia spp., Boophilus spp., Babesia spp., Entamoeba spp., Eimeria spp., Leishmania spp., Schistosome spp., Brugia spp., Fascida spp., Dirofilaria spp., Wuchereria spp., and Onchocerea spp.

Examples of protective antigens of parasitic pathogens include the circumsporozoite antigens of Plasmodium spp. [Sadoff et al., Science 240:336–337 (1988)], such as the circumsporozoite antigen of *P. bergerii* or the circumsporozoite antigen of *P. falciparum;* the merozoite surface antigen of Plasmodium spp. [Spetzler et al., Int. J. Pept. Prot. Res. 43:351–358 (1994)]; the galactose specific lectin of *Entamoeba histolytica* [Mann et al., Proc. Natl. Acad. Sci. USA 88:3248–3252 (1991)], gp63 of Leishmania spp. [Russell et al., J. Immunol. 140:1274–1278 (1988)], paramyosin of *Brugia malayi* [Li et al., Mol. Biochem. Parasitol. 49:315–323 (1991)], the triose-phosphate isomerase of *Schistosoma mansoni* [Shoemaker et al., Proc. Natl. Acad. Sci. USA 89:1842–1846 (1992)]; the secreted globin-like protein of *Trichostrongylus colubriformis* [Frenkel et al., Mol. Biochem. Parasitol. 50:27–36 (1992)]; the glutathione-S-transferase's of *Frasciola hepatica* [Hillyer et al., Exp. Parasitol. 75:176–186 (1992)], *Schistosoma bovis* and *S. japonicum* [Bashir et al., Trop. Geog. Med. 46:255–258 (1994)]; and KLH of *Schistosoma bovis* and *S. japonicum* [Bashir et al., supra].

In the present invention, the live invasive bacteria can also deliver eukaryotic expression cassettes with an alphavirus replicon encoding a therapeutic agent to animal cells or animal tissue.

The eukaryotic expression cassettes with an alphavirus replicon can also encode tumor-specific, transplant, or autoimmune antigens or antigenic parts thereof. Examples of tumor specific antigens include, but are not limited to, prostate specific antigen [Gattuso et al., Human Pathol. 26:123–126 (1995)], TAG-72 and CEA [Guadagni et al., Int. J. Biol. Markers 9:53–60 (1994)], MAGE-1 and tyrosinase [Coulie et al., J. Immunothera. 14:104–109 (1993)]. Recently it has been shown in mice that immunization with non-malignant cells expressing a tumor antigen provides a vaccine effect, and also helps the animal mount an immune response to clear malignant tumor cells displaying the same antigen [Koeppen et al., Anal. N.Y. Acad. Sci. 690:244–255 (1993)]. Hence, a bacterial delivery system for expression of a tumor antigen provides an alternative means to vaccinate a cancer patient.

Examples of transplant antigens include the CD3 receptor on T cells [Alegre et al., Digest. Dis. Sci. 40:58–64 (1995)]. Treatment with an antibody to CD3 receptor has been shown to rapidly clear circulating T cells and reverse most rejection episodes (Alegre et al., supra). Examples of autoimmune antigens include IASβ chain [Topham et al., Proc. Natl. Acad. Sci. USA 91:8005–8009 (1994)]. Vaccination of mice with an 18 amino acid peptide from IASβ chain has been demonstrated to provide protection and treatment to mice with experimental autoimmune encephalomyelitis (Topham et al., supra).

Alternatively, in the present invention, live invasive bacteria can deliver eukaryotic expression cassettes with an alphavirus replicon encoding one or more immunoregulatory molecules. These immunoregulatory molecules include, but are not limited to, growth factors, such as M-CSF, GM-CSF; and cytokines, such as IL-2, IL-4, IL-5, IL-6, IL-10, IL-12 or IFN-gamma. Recently, delivery of cytokines expression cassettes to tumor tissue has been shown to stimulate potent systemic immunity and enhanced tumor antigen presentation without producing a systemic cytokine toxicity [Golumbek et al., Canc. Res. 53:5841–5844 (1993); Golumbek et al., Immun. Res. 12:183–192 (1993); Pardoll, Curr. Opin. Oncol. 4:1124–1129 (1992); and Pardoll, Curr. Opin. Immunol. 4:619–623 (1992)].

The antisense RNA and catalytic RNA species delivered to animal cells can be targeted against any molecule present within the recipient cell or likely to be present within the recipient cell. These include but are not limited to RNA species encoding cell regulatory molecules, such as interleukin-6 [Mahieu et al., Blood 84:3758–3765 (1994)], oncogenes such as ras [Kashani-Sabet et al., Antisen. Res. Devel. 2:3–15 (1992)], causative agents of cancer such as human papillomavirus [Steele et al., Canc. Res. 52:4706–4711 (1992)], enzymes, viral RNA and pathogen-derived RNA such as HIV-1 RNA [Meyer et al., Gene 129:263–268 (1993); Chatterjee et al., Science 258:1485–1488 (1992); and Yamada et al., Virol. 205:121–126 (1994)]. The RNAs can also be targeted at non-transcribed DNA sequences, such as promoter or enhancer regions, or to any other molecule present in the recipient cells, such as but not limited to, enzymes involved in DNA synthesis or tRNA molecules [Scanlon et al., Proc. Natl. Acad. Sci. USA 88:10591–10595 (1991); and Baier et al., Mol. immunol. 31:923–932 (1994)].

In the present invention, live invasive bacteria can also deliver eukaryotic expression cassettes with alphavirus replicons encoding proteins to animal tissue from which such proteins they can later be harvested or purified. An example is the delivery of a eukaryotic expression cassette under the control of a mammary-specific viral promoter, such as derived from mouse mammary tumor virus (ATCC No. VR731), encoding $\alpha_1$-antitrypsin to mammary tissue of a goat or sheep, allowing recovery of the protein from the animal's milk.

Alternatively an invasive bacteria carrying a eukaryotic expression cassette of the invention can be introduced to a tissue site such that it would not spread from such a site. This could be accomplished by any of several methods including delivery of a very limited dose, delivery of a severely attenuated auxotrophic strain, such as an asd mutant (Curtiss et al.(1994), supra) that will be rapidly inactivated or die, or delivery of a bacterial strain that contains attenuating lesions, such as a suicide systems (Rennell et al., supra; and Reader et al., supra) under the control of a strong promoter, such as the anaerobic nirB promoter (Harborne et al., supra) which will be switched on within the recipient host tissue. Additionally, through use of different species and/or serotypes, multiple doses of invasive bacteria carrying the eukaryotic expression cassette of interest can be given to an animal so as to manipulate expression levels or product type. This approach obviates the need for specially-raised transgenic animals containing tissue specific promoters and having tight control of expression, as is currently the case [Janne et al., Int. J. Biochem. 26:859–870 (1994); Mullins et al., Hyperten. 22:630–633 (1993); and Persuy et al., Eur. J. Bichem. 205:887–893 (1992)].

As a further alternative, single or multiple eukaryotic expression cassettes encoding antigens or antigenic fragments, can be delivered in any single or multiple combination with eukaryotic expression cassettes encoding immunoregulatory molecules or other proteins.

The invasive bacteria containing the eukaryotic expression cassette of the invention can be used to infect animal cells that are cultured in vitro. The animal cells can be further cultured in vitro, and the cells carrying the desired genetic trait can be enriched by selection for or against any selectable marker introduced to the recipient cell at the time of infection, also referred to as bactofection. Such markers may include antibiotic resistance genes, e.g., hygromycin, or neomycin, selectable cell surface markers, or any other phenotypic or genotypic element introduced or altered by bactofection. These in vitro-infected cells or the in vitro-enriched cells can then be introduced into animals intravenously, intramuscularly, intradermally, or intraperitoneally, or by any inoculation route that allows the cells to enter the host tissue and express the heterologous nucleic acid sequences of interest. Alternatively, these in vitro-infected cells can be used for production and recovery of the gene product encoded by the heterologous nucleic acid.

To infect animals with the live, invasive bacteria containing the eukaryotic expression cassettes of the invention, the bacteria can be introduced by intravenous, intramuscular, intradermal, intraperitoneally, peroral, intranasal, intraocular, intrarectal, intravaginal, oral, immersion and intraurethral inoculation routes.

The amount of the live invasive bacteria of the present invention to be administered will vary depending on the species of the subject, as well as the disease or condition that is being treated. Generally, the dosage employed will be about $10^3$ to $10^{11}$ viable organisms, preferably about $10^5$ to $10^9$ viable organisms. Alternatively, when bactofecting individual cells, the dosage of viable organisms to administered will be at a multiplicity of infection ranging from about 0.1 to $10^6$, preferably about $10^2$ to $10^4$.

The invasive bacteria of the present invention are generally administered along with a pharmaceutically acceptable carrier or diluent.

The particular pharmaceutically acceptable carrier or diluent employed is not critical to the present invention. Examples of diluents include a phosphate buffered saline, buffer for buffering against gastric acid in the stomach, such as citrate buffer (pH 7.0) containing sucrose, bicarbonate buffer (pH 7.0) alone [Levine et al., J. Clin. Invest. 79:888–902 (1987); and Black et al, J. Infect. Dis. 155:1260–1265 (1987)], or bicarbonate buffer (pH 7.0) containing ascorbic acid, lactose, and optionally aspartame [Levine et al., Lancet II:467–470 (1988)]. Examples of carriers include proteins, e.g., as found in skim milk; sugars, e.g., sucrose; or polyvinylpyrrolidone. Typically these carriers would be used at a concentration of about 0.1–90% (w/v) but preferably at a range of 1–10% (w/v).

When infecting animal cells, the methods of the invention can be used in mammalian, avian, insect cells and the like. Preferably the mammalian cells are selected from the group consisting of human, bovine, ovine, porcine, feline, buffalo, canine, goat, equine, donkey, deer, and primate cells.

When infecting animals, the methods of the invention are preferably used in mammals and birds. The preferred mammal is a human.

What is claimed is:

1. A bacterial delivery system which comprises live invasive bacteria containing a DNA comprising a eukaryotic expression cassette operably linked to an alphavirus replicon DNA capable of amplification as RNA in animal cells, wherein the alphavirus replicon DNA comprises at least one nucleic acid control sequence operably linked to a heterologous nucleic acid sequence to control expression of said heterologous gene.

2. The bacterial delivery system of claim 1, wherein said bacteria are attenuated.

3. The bacterial delivery system of claim 1, wherein said heterologous nucleic acid sequence comprises one or more coding regions of a gene.

4. The bacterial delivery system of claim 3, wherein each coding region of said heterologous nucleic acid sequences can be expressed separately or as an operon.

5. The bacterial delivery system of claim 1, wherein said heterologous nucleic acid sequence encodes an antigen, an antigenic fragment of a protein, a therapeutic agent, an immunoregulatory agent, an anti-sense RNA, a catalytic RNA, a protein, a peptide, an antibody or an antigen-binding fragment of an antibody.

6. The bacterial delivery system of claim 5, wherein said antigen or said antigenic fragment of a protein is from a viral pathogen, a bacterial pathogen or a parasitic pathogen.

7. The bacterial delivery system of claim 1, wherein the heterologous nucleic acid sequence is a viral sequence from a virus selected from the group consisting of influenza virus, respiratory syncytial virus, HPV, HBV, HCV, HIV, HSV, FeLV, FIV, HTLV-I, HTLV-II, and CMV.

8. The bacterial delivery system of claim 7, wherein the viral sequences encode one or more viral genes or antigenic fragments of a protein encoded by said genes.

9. The bacterial delivery system of claim 7, wherein said virus is HIV.

10. The bacterial delivery system of claim 9, wherein said heterologous nucleic acid sequence encodes one or more HIV genes selected from the group consisting of env, gag, pol, nef, tat, or rev or an antigenic fragment of a protein encoded by any one of said genes.

11. The bacterial delivery system of claim 10, wherein said heterologous nucleic acid sequence encodes at least one antigen or antigenic fragment from each of the HIV genes env, gag, pol, nef, tat, and rev.

12. The bacterial delivery system of claim 10 or 11, wherein said HIV gene is from an HIV isolate or from a consensus sequence of HIV isolates.

13. The bacterial delivery system of claim 5, wherein said antigen or said antigenic fragment of a protein is a tumor antigen, a transplantation antigen or an autoimmune antigen.

14. The bacterial delivery system of claim 1, wherein the heterologous nucleic acid sequence encodes a cytokine, an interleukin, erythropoietin, or other immunostimulatory or immunoregulatory protein.

15. A method for introducing and expressing a gene in an animal which comprises infecting said animal with live invasive bacteria containing a DNA comprising a eukaryotic expression cassette operably linked to an alphavirus replicon DNA capable of amplification as RNA in animal cells, wherein the alphavirus replicon DNA comprises at least one nucleic acid control sequence operably linked to a heterologous nucleic acid sequence to control expression of said heterologous nucleic acid, and thereby obtaining expression of a gene product encoded by said heterologous nucleic acid sequence in said animal.

16. The method of claim 15, wherein said bacteria are attenuated.

17. The method of claim 15, wherein said heterologous nucleic acid sequence comprises one or more coding regions of a gene.

18. The method of claim 15, wherein said gene product is an antigen, an antigenic protein fragment, a therapeutic agent, an immunoregulatory agent, an anti-sense RNA, a catalytic RNA, a protein, a peptide, an antibody or an antigen-binding fragment of an antibody.

19. The method of claim 18, wherein said antigen or said antigenic fragment of a protein is from a viral pathogen, a bacterial pathogen or a parasitic pathogen.

20. The method of claim 18, wherein said antigen or said antigenic fragment of a protein is a tumor antigen, a transplantation antigen or an autoimmune antigen.

21. The method of claim 15, wherein the heterologous nucleic acid sequence is a viral sequence from a virus selected from the group consisting of influenza virus, respiratory syncytial virus, HPV, HBV, HCV, HIV, HSV, FeLV, FIV, HTLV-I, HTLV-II, and CMV.

22. The method of claim 21, wherein said virus is HIV.

23. The method of claim 15, wherein the heterologous nucleic acid sequence encodes a cytokine, an interleukin, erythropoietin, or other immunostimulatory or immunoregulatory protein.

24. The method of claim 15 wherein infecting occurs by an intranasal delivery route.

25. A method for inducing an immune response in an animal which comprises infecting said animal with live invasive bacteria containing a DNA comprising a eukaryotic expression cassette operably linked to an alphavirus replicon DNA capable of amplification as RNA in animal cells, wherein the alphavirus replicon DNA encodes at least one antigen or antigenic fragment of a protein, and wherein said antigen or said fragment is expressed at a level sufficient to stimulate an immune response to said antigen or said fragment.

26. The method of claim 25, wherein said bacteria are attenuated.

27. The method of claim 25, wherein said antigen or said antigenic fragment is a tumor antigen, a transplantation antigen or an autoimmune antigen.

28. The method of claim 25, wherein said antigen or said antigenic fragment of a protein is from a viral pathogen, a bacterial pathogen or a parasitic pathogen.

29. The method of claim 25, wherein the antigen or antigenic fragment is from a virus selected from the group consisting of influenza virus, respiratory syncytial virus, HPV, HBV, HCV, HIV, HSV, FeLV, FIV, HTLV-I, HTLV-II, and CMV.

30. The method of claim 29, wherein said virus is HIV.

31. The method of claim 30, wherein said antigen or antigenic fragment is encoded by an HIV gene selected from the group consisting of env, gag, pol, nef, tat, or rev.

32. The method of claim 31, wherein said alphavirus replicon DNA encodes at least one antigen or antigenic fragment from each of the HIV genes env, gag, pol, nef, tat, and rev.

33. The method of claim 31 or 32, wherein said HIV gene is from an HIV isolate or from a consensus sequence of HIV isolates.

34. The method of claim 25 wherein infecting occurs by an intranasal delivery route.

35. A method for introducing and expressing a gene in animal cells comprising (a) infecting said animal cells with live invasive bacteria containing one or more DNA molecules, said molecules comprising a eukaryotic expression cassette operably linked to an alphavirus replicon DNA capable of amplification as RNA in said cells, wherein the alphavirus replicon DNA comprises at least one nucleic acid control sequence operably linked to a heterologous nucleic acid sequence to control expression of a gene product encoded by said heterologous nucleic acid sequence; and (b) culturing those cells under conditions sufficient to express said gene product.

36. The method of claim 35, wherein said bacteria are attenuated.

37. The method of claim 35, wherein said heterologous nucleic acid sequence comprises one or more coding regions of a gene.

38. The method of claim 37, wherein each coding region of said heterologous nucleic acid sequences can be expressed separately or as an operon.

39. The method of claim 35, wherein said heterologous nucleic acid sequence encodes an antigen, an antigenic fragment of a protein, a therapeutic agent, an immunoregulatory agent, an anti-sense RNA, a catalytic RNA, a protein, a peptide, an antibody or an antigen-binding fragment of an antibody.

40. The method of claim 39, wherein said antigen or said antigenic fragment of a protein is a tumor antigen, a transplantation antigen or an autoimmune antigen.

41. The method of claim 35, wherein the heterologous nucleic acid sequence encodes a cytokine, an interleukin, erythropoietin, or other immunostimulatory or immunoregulatory protein.

42. The method of claim 39, wherein said antigen or said antigenic fragment of a protein is from a viral pathogen, a bacterial pathogen or a parasitic pathogen.

43. The method of claim 35, wherein the heterologous nucleic acid sequence is a viral sequence from a virus selected from the group consisting of influenza virus, respiratory syncytial virus, HPV, HBV, HCV, HIV, HSV, FeLV, FIV, HTLV-I, HTLV-II, and CMV.

44. The method of claim 43, wherein the viral sequences encode one or more viral genes or antigenic fragments of a protein encoded by said genes.

45. The method of claim 43, wherein said virus is HIV.

* * * * *